(12) United States Patent
Nielsen et al.

(10) Patent No.: US 6,734,241 B1
(45) Date of Patent: May 11, 2004

(54) COMPOSITION

(75) Inventors: Bjarne Nielsen, Hovedgard (DK); Flemming Vang Sparso, Skanderborg (DK); Jorgen Kirk Kristiansen, Vejle (DK)

(73) Assignee: Danisco A/S., Copenhagen (DK)

( * ) Notice: Subject to any disclaimer, the term of this patent is extended or adjusted under 35 U.S.C. 154(b) by 298 days.

(21) Appl. No.: 09/642,480

(22) Filed: Aug. 18, 2000

Related U.S. Application Data

(63) Continuation-in-part of application No. PCT/IB00/01773, filed on Aug. 9, 2000.
(60) Provisional application No. 60/167,923, filed on Nov. 29, 1999.

(30) Foreign Application Priority Data

Aug. 19, 1999 (GB) ............................................... 9919683

(51) Int. Cl.$^7$ ................................................. C08K 5/10
(52) U.S. Cl. ...................... 524/287; 524/306; 524/311; 524/312; 524/313; 524/504; 524/563; 524/567; 524/568; 524/569; 568/300; 568/303
(58) Field of Search ................................. 524/287, 306, 524/311, 312, 313, 504, 563, 567, 568, 569; 568/300, 303

(56) References Cited

U.S. PATENT DOCUMENTS

| | | | |
|---|---|---|---|
| 3,388,104 A | 6/1968 | Crovatt | |
| 4,426,477 A | * 1/1984 | Yasumatsu et al. | ......... 524/306 |
| 4,637,887 A | 1/1987 | Worschech et al. | |

FOREIGN PATENT DOCUMENTS

| | | |
|---|---|---|
| CH | 512 546 | 9/1971 |
| GB | 1139646 | 12/1965 |
| GB | 1164750 | 6/1967 |
| WO | WO 92/00349 | 1/1992 |

OTHER PUBLICATIONS

Jain, A. K. et al (1972) J. "Evaluation of plasticisation characteristics of acylated/ aroylated monoricinoleins for P.V.C. resins" J. Oil Technol. Ass. India vol. 4, No. 1, p. 27–32.
Chandran, D.V. et al (1970) "Acylated Monoricinoleates as Plasticizers for polyvinyl Chloride Resins" Indian J. Technol. vol. 8, No. 4, p. 143–145.
Jain, A.K. et al (1970) "Acetylated glycol ricinoleate as primary plasticizers for polyvinyl resins" J. Oil. Technol. Ass. India vol. 2, No. 1, pp. 12–15.
Singh, S. et al (1969) "Castor oil based potential primary plasticizers for polyvinyl chloride resins" Popular Plastics Jul. 1969, p. 39–44.
Teupel et al (1968) "Analysis of Ricinoleic Acid Monoglycerides by means of Column Chromatography and nuclear Resonance Spectroscopy" Tenside, No. 9/10 p. 275–278.

* cited by examiner

*Primary Examiner*—William Cheung
(74) *Attorney, Agent, or Firm*—Frommer Lawrence & Haug; Thomas J. Kowalski

(57) ABSTRACT

There is provided composition comprising i) a thermoplastic polymer ii) a compound having the formula

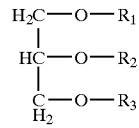

wherein $R_1$, $R_2$ and $R_3$ are independently selected from an acyl group or a hydrogen atom, wherein at least one of $R_1$, $R_2$ and $R_3$ is an acyl group (a short acyl group) having from 2 to 6 carbon atoms, wherein at least one of $R_1$, $R_2$ and $R_3$ is a branched chain acyl group (a long acyl soup) consisting of a saturated chain having 10 to 20 carbon atoms and a hydrophilic branch group.

20 Claims, No Drawings

COMPOSITION

This application is a continuation-in-part of Danisco A/S or Nielsen, PCT/IB00/01773, filed Aug. 9, 2000 with the International Bureau of WIPO designating the United States. This application also claims priority from U.S. application Ser. No. 60/167,923 filed Nov. 29, 1999 and United Kingdom Application Serial No. 60/167,923 filed Aug. 19, 1999. Each of these applications and patent and each document cited or referenced in each of these applications and patents, including during any prosecution ("application cited documents"), and each document cited or referenced in each of the application cited documents, are hereby incorporated herein by reference. In addition, each document cited in this text ("herein cited documents") and each document cited or referenced in each of the herein cited documents, and each product data sheet for each commercially available product mentioned herein, are hereby incorporated herein by reference.

The manufacturing properties of thermoplastic polymers, for example the extruding properties of such polymers, is often modified/enhanced by the addition of plasticisers thereto. As acknowledged in the prior art, such as in U.S. Pat. No. 4,426,477, there is a tendency toward avoiding the commonly used plasticisers such as dioctyl adipate (DOA) and phthalate plasticisers such as dioctyl phthalate (DOP). The safety of these plasticisers has been called into question, particularly in certain applications.

U.S. Pat. No. 4,426,477 discloses plasticisers based on glycerol esters. The plasticisers consist of compounds prepared by the acylation of glycerol. The compounds comprises triesters, wherein approximately two of the acyls have two carbons and the remaining one acyl has from 10 to 14 carbons. The compounds of U.S. Pat. No. 4,426,477 provide a plasticising effect. However, in certain applications the plasticisers have a volatility such that they may migrate out of the thermoplastic polymer in which they are incorporated, such as PVC.

In a first aspect the present invention provides a composition comprising i) a thermoplastic polymer ii) a compound having the formula

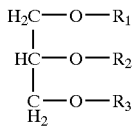

wherein $R_1$, $R_2$ and $R_3$ are independently selected from an acyl group or a hydrogen atom, wherein at least one of $R_1$, $R_2$ and $R_3$ is an acyl group (a short acyl group) having from 2 to 6 carbon atoms, wherein at least one of $R_1$, $R_2$ and $R_3$ is a branched chain acyl group (a long acyl group) consisting of or having a saturated chain having 10 to 20 carbon atoms and a hydrophilic branch group.

Preferably two of $R_1$, $R_2$ and $R_3$ are short acyl groups as described above and the other of $R_1$, $R_2$ and $R_3$ is a long acyl group as described above. In this aspect, the compound may be of the formula

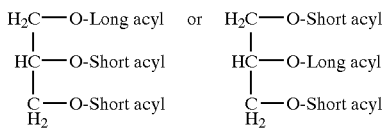

Preferably the hydrophilic branch group is a group selected from acyl and derivatives thereof. Preferred derivatives include groups of the formula —O-acyl.

Preferably the hydrophilic branch group is a group of the formula

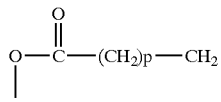

wherein p is from 0 to 4 or 0 to 3.

In a preferred aspect of the present invention the chain of the long acyl group consists of or has a saturated chain having 14 to 20 carbon atoms. In a more preferred aspect, the chain of the long acyl group consists of or has a saturated chain having 16 to 20 carbon atoms Preferably the long acyl group is of the formula

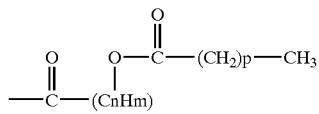

wherein n is from 10 to 20 and m is 2n, and wherein p is from 0 to 4 or 0 to 3.

Preferably n is from 16 to 20, more preferably from 16 to 18, yet more preferably 17.

Preferably the group CnHm is a straight chain hydrocarbon group.

In a highly preferred aspect the long acyl group is a group of the formula

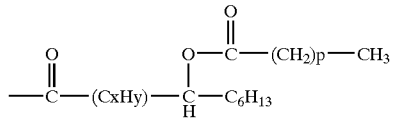

wherein x is from 7 to 10, preferably x is 10, and y is 2x, and wherein p is from 0 to 4 or 0 to 3, preferably p is 0.

Preferably the group CxHy is or comprises a straight chain hydrocarbon group.

In a highly preferred aspect the long acyl group is a group of the formula

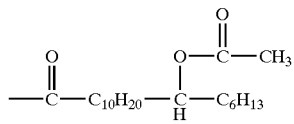

In a preferred aspect of the present invention the short acyl group is or comprises an acyl group having from 2 to 5 carbon atoms. In a more preferred aspect, the short acyl group is or comprises an acyl group having 2 carbon atoms. The short acyl group is preferably of the formula

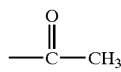

Preferably the short acyl group and the hydrophilic branch group contain the same number of carbon atoms. In a highly preferred aspect the hydrophilic branch group is a group of the formula

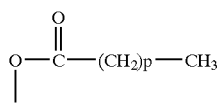

and the short acyl group is of the formula

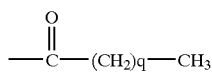

wherein p=q and is from 0 to 4 or 0 to 3.

In certain aspects, it is desirable for the short acyl groups to be present in a maximum amount with respect to the total amount glycerol and esters thereof present in the composition. Preferably the short acyl group is present in an amount on average, of no greater than 2 moles per mole of glycerol and esters thereof present in the composition.

In certain aspects, it is desirable for the long acyl groups to be present in a minimum amount with respect to the total amount glycerol and esters thereof present in the composition. Preferably the long acyl group is present in an amount, on average, of at least 0.4 moles, preferably from 0.9 to 2 moles, more preferably from 0.9 to 1 moles per mole of glycerol and esters thereof present in the composition.

It may also be preferred for the majority of the glycerol present in the composition to be fully acylated Accordingly, in a preferred aspect the total amount of acyl groups is, on average, 2.7 to 3.0 moles per mole of glycerol and esters thereof The compound of the present invention may be prepared by interesterification between glycerol and one or more oils, including natural oils and hardened natural oils followed by acylation. Thus, the compound of the present invention may be the product of a two part process comprising (i) an interesterification between glycerol and an oil selected from castor oil, including hardened castor oil, unhardened castor oil and mixtures thereof, and (ii) acylation.

Thus in a further aspect the present invention provides a process for the preparation of a compound having the formula

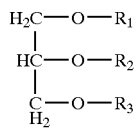

wherein $R_1$, $R_2$ and $R_3$ are independently selected from an acyl group or a hydrogen atom; wherein at least one of $R_1$, $R_2$ and R3 is an acyl group (a short acyl group) having from 2 to 6 carbon atoms or from 2 to 5 carbons; wherein at least one of $R_1$, $R_2$ and $R_3$ is a branched chain acyl group (a long acyl group) consisting of or having a chain having 10 to 20 carbon atoms and a hydrophilic branch group; the process comprising the steps of:
  (i) interesterification between glycerol and triglyceride compound having the formula

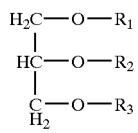

wherein each of $R_1$, $R_2$ and $R_3$ is a fatty acid group consisting of or having a chain having 10 to 20 carbon atoms, to provide a composition comprising glycerol, monoglyceride, diglyceride and/or triglyceride;
  (ii) optionally isolating the monoglyceride and/or diglyceride from the composition;
  (iii) acylating the monoglyceride and/or diglyceride or the composition containing the same.

In the process of the present invention the chain having 10 to 20 carbon may be saturated or unsaturated.

The process of the present invention may utilise, for example, castor oil or hardened castor oil. The compound of the present invention may be prepared from hardened castor oil. A typical fatty acid profile of castor oil and hardened castor oil is given below.

| Fatty Acid | Content [%] |
|---|---|
| Castor Oil | |
| Palmitic (C16) | 1.0 |
| Stearic (C18) | 1.1 |
| Oleic (C18:1) | 3.8 |
| Linoleic (C18:2) | 4.4 |
| Linolenic (C18:3) | 0.5 |
| Gadoleic (C20:1) | 0.5 |
| Ricinoleic (C18:1–OH) | 87.4 |
| Hardened Castor Oil | |
| Palmitic (C16) | 1.3 |
| Stearic (C18) | 9.3 |
| Oleic (C18:1) | 0.9 |
| Linoleic (C18:2) | 0.2 |
| Arachidic (C20) | 0.7 |
| Ricinoleic hard (C18–OH) | 84.9 |

The nomenclature in parenthesis is Cxx:y where xx is the fatty acid carbon number and y indicates number of double bonds. Ricinoleic acid, hard (also known as 12-hydroxy stearic acid) has a hydroxyl group (OH) on the $12^{th}$ carbon.

In this aspect the product based on the castor oil, or indeed a product based on another oil, may be synthesised as follows. These synthetic routes are given by way of example only. Other routes would be appreciated by a person skilled in the art Route 1

Castor oil and glycerol are reacted to produce an equilibrium mixture of different glycerol esters. This mixture can be distilled and subsequently acetylated to provide the desired end products. This route is illustrated below.

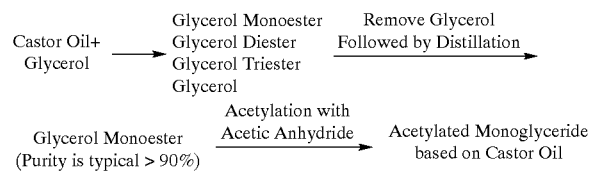

The second, step comprising the removal of the glycerol followed by distillation is optional. In other word the mixture of glycerol, glycerol monoester, glycerol diester, and glycerol triester may directly acetylated with acetic anhydride to form a mixture of acetylated products. The acetylated monoglyceride or the mixture of acetylated products may have a yellowish color. The yellowish product may be distilled. The distilled product is clear.

Depending on the ratio between castor oil and glycerol and depending on the reaction conditions, the described process provides different glycerol ester mixtures. The glycerol monoester is typically 45–65% and may be up to 65%. This is achieved in a typical reaction mixture. Such a composition may then, optionally, be fir processed to provide a product having a higher purity, for example a monoester content of above 90%.

Typical further processing would involve the removal of glycerol and the subsequent distillation of the resulting mixture. By means of this further processing an end product with a typical glycerol monoester content above 90% may be provided. The fatty acid profile of the end product would reflect the fatty acid profile of the castor oil stating material. This process, namely the production of a glycerol monoester, is described in Bailey's Industrial Oil & Fat Products, vol. 4, Fifth ed. P.572 ff The glycerol monoester may then be reacted with an excess of acetic anhydride resulting in acetic acid being esterified with the glycerol ester. Any excess of acetic anhydride is removed from the reaction mixture. The end product is a fully acetylated monoglyceride based on castor oil (which may be hardened or unhardened castor oil).

Route 2

Route 2 provides a further manner in which acetylated monoglycerides based on, for example, hardened and unhardened castor oil may be synthesised. An acetylated monoglyceride may be produced by the reaction of castor oil with acetic anhydride to provide an acetylated castor oil, The acetylated castor oil is then reacted with triacetin to produce acetylated monoglycerides based on hardened and unhardened castor oil. This process is illustrated below.

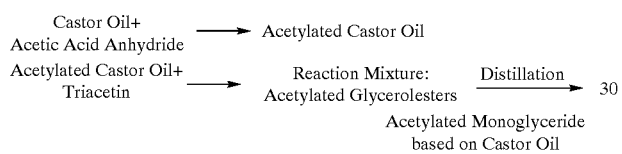

Castor oil is reacted with acetic anhydride to produce an acetylated castor oil. The degree of acetylation may be defined as castor oil containing at least one acetic acid group and up to the average of three acetic acid groups per mole of castor oil. The acetylated castor oil is then reacted with triacetin to produce a reaction mixture of mainly acetylated glycerolesters with a fatty acid profile similar to that of the castor oil starting material. This mixture is purified by distillation. The end product is an acetylated monoglyceride based on hardened or unhardened castor oil.

A process for obtaining acetylated glycerol esters from the reaction of a triglyceride and triacetin is described in the Danish Patent No. 93 786. The synthesis of acetylated monoglycerides based on castor oil from the starting materials acetylated castor oil and triacetin is analogous to that process.

In a highly preferred aspect the compound of the present invention is selected from compounds of the formula

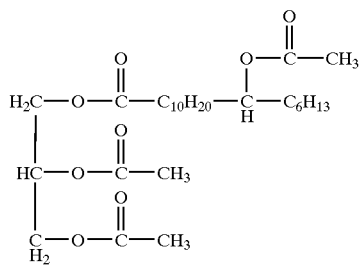

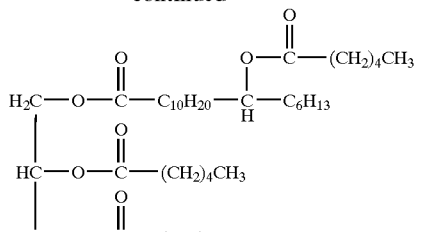

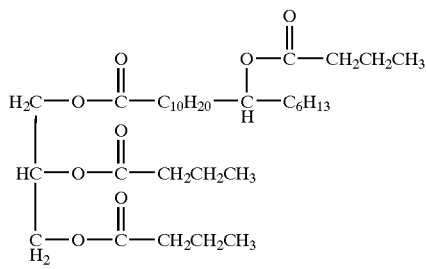

These preferred compounds may be prepared and are preferably prepared in accordance with Route 1 or Route 2 above.

The above compounds are specific compounds which may be provided by the present invention. In a broad aspect, the present invention further provides a compound of the formula

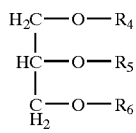

wherein two of $R_4$, $R_5$, and $R_6$ are of the formula

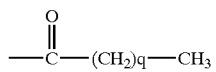

wherein for each of the two of $R_4$, $R_5$, and $R_6$ q is independently selected from 0 to 4 or from 0 to 3; and the other of $R_4$, $R_5$, and $R_6$ is a branched group of the formula

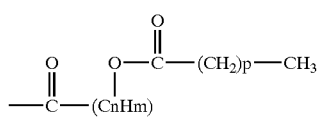

wherein n is from 10 to 20 and m is 2 n, and wherein p is from 0 to 4 or from 0 to 3.

Preferably q is 0. More preferably for both of the two of $R_4$, $R_5$, and $R_6$ q is 0.

Preferably n is from 16 to 20, more preferably from 16 to 18, yet more preferably 17.

Preferably the group CnHm is a straight chain hydrocarbon group.

In a preferred aspect the branched group is a group of the formula

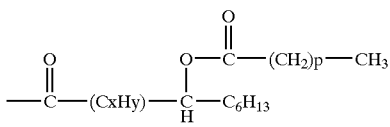

wherein x is from 7 to 10, preferably x is 10, and y is 2x, and wherein p is from 0 to 4 or from 0 to 3, preferably p is 0.

Preferably the group CxHy is a straight chain hydrocarbon group.

The compounds provided by the present invention may be incorporated in a composition comprising a thermoplastic polymer. Accordingly in a further aspect the present invention provides a composition comprising a compound as defined above and a thermoplastic polymer.

The thermoplastic polymer of the compositions of the present invention may be or comprise a vinyl chloride polymer or a vinyl chloride copolymer selected from vinyl chloride/vinyl acetate copolymer, vinyl chloride/vinylidene chloride copolymer, vinyl chloride/ethylene copolymer and a copolymer prepared by grafting vinyl chloride onto ethylene/vinyl acetate copolymer, or a mixture thereof.

In a preferred aspect the thermoplastic polymer is or comprises a polymer blend of a thermoplastic polymer, preferably a thermoplastic polymer as defined above, and a second polymer. Preferably, the second polymer is a methacryl polymer or an acrylonitrile-butadiene-styrene polymer.

The compositions of the present invention may be formulated in any manner to provide the required plasticising properties of the compound. In a particular aspect the composition of the present invention comprises the compound in an amount of 1 to 100 parts by weight per 100 parts by weight of the thermoplastic polymer.

PROCESS OF INVENTION

As disclosed above the present invention provides a process for the preparation of a compound having the formula

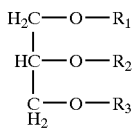

wherein $R_1$, $R_2$ and $R_3$ are independently selected from an acyl group or a hydrogen atom, wherein at least one of $R_1$, $R_2$ and $R_3$ is an acyl group (a short acyl group) having from 2 to 5 or from 2 to 6 carbon atoms, wherein at least one of $R_1$, $R_2$ and $R_3$ is a branched chain acyl group (a long acyl group) consisting of or having a chain having 10 to 20 carbon atoms and a hydrophilic branch group, the process comprising the steps of: (i) interesterification between glycerol and triglyceride compound having the formula

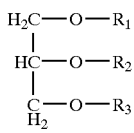

wherein each of $R_1$, $R_2$ and $R_3$ is a fatty acid group consisting of or having a chain having 10 to 20 carbon atoms, to provide a composition comprising glycerol, monoglyceride, diglyceride and/or triglyceride; (ii) optionally isolating the monoglyceride and/or diglyceride from the composition; (iii) acylating the monoglyceride and/or diglyceride or the composition containing the same.

In the process of the present invention the chain having 10 to 20 carbon atoms may be saturated or unsaturated.

In preferred aspects the compound prepared by the process is a compound of the present invention as described herein. In a broader aspects the long acyl group is of the formula

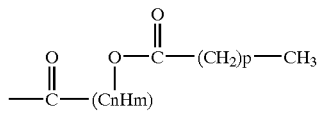

wherein n is from 10 to 20 and m is selected from 2n, 2n−2, 2n−4 and 2n−6, and wherein p is from 0 to 4 or from 0 to 3.

Preferably m is 2n or 2n−2.

Preferably the group CnHm is a straight chain hydrocarbon group. The straight chain hydrocarbon group may be saturated or unsaturated. The straight chain hydrocarbon group may contain a single —C=C— bond.

the long acyl group is a group of the formula

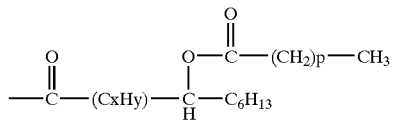

wherein x is from 7 to 10, preferably x is 10, and y is 2x−2, and wherein p is from 0 to 4 or from 0 to 3, preferably p is 0.

Preferably the group CxHy is a straight chain hydrocarbon group. The straight chain hydrocarbon group may be saturated or unsaturated. The straight chain hydrocarbon group may contain a single —C=C— bond.

the long acyl group is a group of the formula

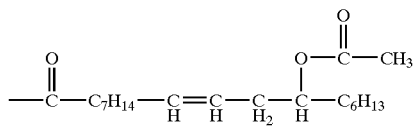

the compound is of the formula

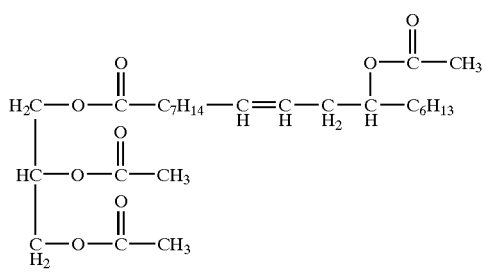

the compound is of the formula

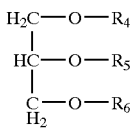

wherein two of $R_4$, $R_5$, and $R_6$ are of the formula

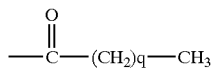

wherein for each of the two of $R_4$, $R_5$, and $R_6$ q is independently selected from 0 to 4 or from 0 to 3 and the other of $R_4$, $R_5$, and $R_6$ is a branched group of the formula

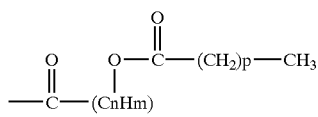

wherein n is from 10 to 20 and m is selected from 2n, 2n−2, 2n−4 and 2n−6, and wherein p is from 0 to 4 or from 0 to 3. Preferably q is 0. More preferably for both of the two of $R_4$, $R_5$, and $R_6$ q is 0. Preferably n is from 16 to 20, more preferably from 16 to 18, yet more preferably 17. Preferably m is 2n−2.

the branched group is a group of the formula

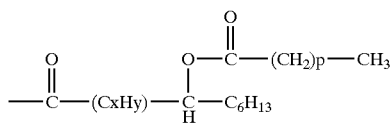

wherein x is from 7 to 10, preferably x is 10, and y is 2x—2, and wherein p is from 0 to 4 or from 0 to 3, preferably p is 0.

The invention will now be described in further detail with in the following Examples.

EXAMPLES

Plasticisers Evaluated

Six plasticisers were evaluated. These were:

1. dioctyl phthalate (DOP)—a conventional phthalate based plasticiser. DOP is by far the most widely used plasticiser for PVC DOP is available from Monsanto Europe, Belgium
2. Diisononyl phthalate (DINP)—a conventional phthalate based plasticiser from Monsanto Europe, Belgium
3. Compound A—a compound having the structure

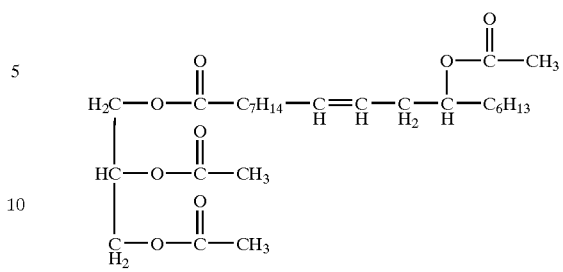

4. Compound B—a compound having the structure

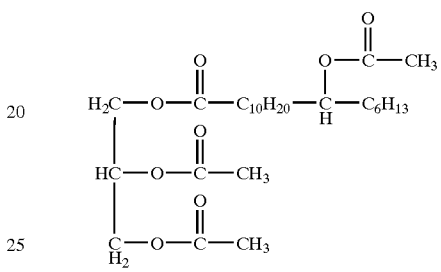

5. Compound C—a compound having the structure.

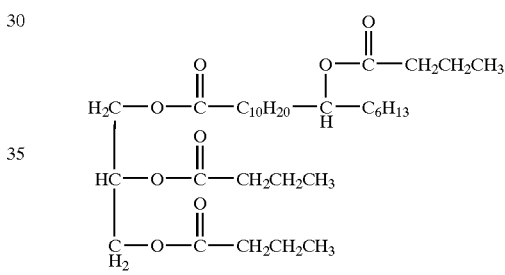

6. Compound D—a compound having the structure

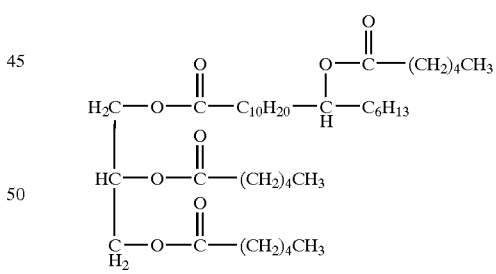

DOP, DINP and compound A are comparative compounds not in accordance with the compound/composition of the present invention. Compounds B, C and D are compounds containing saturated longs chains in accordance with the present invention.

Synthesis

The compounds were prepared as follows.
Synthesis of Compound A (Process of the Invention)
100 gram of castor oil, 30 gram of glycerol and 0.3 gram of 50% sodium hydroxide is heated to 250° C. and reacted for 60 minutes. The sodium hydroxide is neutralised with 0.5 gram of 85% phosphoric acid. The glycerol is removed by water vapour distillation at 140° C. and 0.05 mbar. The monoglyceride is concentrated by short path distillation at 200° C. and a pressure below $5*10^{-3}$ mbar. 40 gram of monoglyceride is then reacted with 40 grain of acetic anhydride at 140° C. for 60 minutes and the formed acetic acid is removed by vacuum distillation. The yield of compound A is 50 gram.

The synthesis provided a composition (Composition A) containing approximately 90 wt. % of a plasticiser compound A.

Synthesis of Compound B (Compound of the Invention)

100 gram of hydrogenated castor oil is reacted with 32 gram of acetic anhydride at 140° C. for 60 minutes and the formed acetic acid is removed by vacuum distillation. 100 gram of the fully acetylated hydrogenated castor oil is reacted with 100 gram of triacetin, 0.0045 of sodium methoxide and 0.825 gram of aluminium stearate at 250° C. for 60 minutes. The non reacted triacetin is removed by vacuum distillation at 135° C. and 0.01 mbar. Compound B is concentrated by short path distillation at 200° C. and a pressure below $5*10^{-3}$ mbar. The yield of compound B is 40 gram.

The synthesis provided a composition (Composition B) containing approximately 90 wt. % of a plasticiser compound B.

Synthesis of Compound C (Compound and Process of the Invention)

100 gram of hydrogenated castor oil, 30 gram of glycerol and 0.3 gram of 50% sodium hydroxide is heated to 250° C. and reacted for 60 minutes. The sodium hydroxide is neutralised with 0.5 gram of 85% phosphoric acid. The glycerol is removed by water vapour distillation at 140° C. and 0.05 mbar. The monoglyceride is concentrated by short path distillation at 200° C. and a pressure below $5*10^{-3}$ mbar. 40 gram of monoglyceride is then reacted with 54 gram of butyric anhydride at 150° C. for 90 minutes and the formed butyric acid is removed by vacuum distillation. The yield of compound C is 61 gram.

The synthesis provided a composition (Composition C) containing plasticiser compound C.

Synthesis of Compound D (Compound and Process of the Invention)

100 gram of hydrogenated castor oil, 30 gram of glycerol and 0.3 gram of 50% sodium hydroxide is heated to 250° C. and reacted for 60 minutes. The sodium hydroxide is neutralised with 0.5 gram of 85% phosphoric acid. The glycerol is removed by water vapour distillation at 140° C. and 0.05 mbar. The monoglyceride is concentrated by short path distillation at 200° C. and a pressure below $5*10^{-3}$ mbar. 40 gram of monoglyceride is then reacted with 74 gram of hexanoic acid anhydride at 160° C. for 90 minutes and the formed hexanoic acid is removed by vacuum distillation. The yield of compound D is 67 gram.

The synthesis provided a composition (Composition D) containing plasticiser compound D.

Example 1

Plasticiser composition 3 is tested for its function as a plasticiser using the following formulation.

| Formulation | |
|---|---|
| PVC (K = 70), Vestolit S7054* | 100 parts by weight |
| Ca—Zn stabilizer | 1 parts by weight |
| Epoxidised soybean oil | 3 parts by weight |
| Plasticiser composition | 50 parts by weight |

*available from Hüls AG, Germany

Test Procedure

A predetermined amount of plasticiser composition is added to the above formulation and the mixture kneaded at 150 to 155° C. for 5 minutes between 20 cm test rollers. The rolled sheet is further pressed at 160° C. and 150 kg/cm² using a compression molding machine to form a 1-mm thick sheet.

The test procedure demonstrates that Composition B provides a plasticising effect.

Example 2

Plasticiser composition B and the four plasticisers of Example 2 of U.S. Pat. No. 4,426,477 are tested for their function as a plasticiser using a PVC paste resin formulation.

| Formulation | |
|---|---|
| PVC (K = 78), Vestolit P1348K* | 100 parts by weight |
| Ca—Zn liquid stabiliser | 3 parts by weight |
| Plasticiser composition | 60 parts by weight |

*available from Hüls AG, Germany

Test Procedures

Bleeding Property—after dearation the compositions are spread over a glass plate to form a 1 mm thick film. The film is allowed to gel for 15 minutes in an oven at 180° C. The resulting sheet is left to stand at room temperature for a week. The bled matter is washed off with an acetone/IPA mixture. The sheet is dried to measure its weight loss.

The test procedure demonstrates that Composition B bleeds less than each of the compositions of U.S. Pat. No. 4,426,477.

Example 3

Plasticiser composition B is evaluated by using an ethylene/vinyl chloride copolymer sheet formulation.

| Formulation | |
|---|---|
| Ethylene/vinyl copolymer (K = 55)* | 100 parts by weight |
| Ca—Zn stabiliser | 2.0 parts by weight |
| Methylmethacryl-butadiene-styrene resin | 5.0 parts by weight |
| Lubricant, stearic acid monoglyceride | 1.0 parts by weight |
| Polyethylene wax | 0.3 parts by weight |
| Plasticiser composition | 3.0 parts by weight |

*available from Hüls AG, Germany

Test Procedure

The above formulation is kneaded at 180 to 190° C. for 5 minutes between 20 cm test rollers. The processability is judged at this point. Next, the rolled sheet is further pressed at 180° C. and 100 kg/cm² to form a 1 mm thick sheet, and then the transparency is measured.

The test procedure demonstrates that Composition B provides a polymer composition having good processability and good transparency.

Example 4

Plasticiser composition B is evaluated by using a PVC wrap formulation.

| Formulation | |
|---|---|
| PVC (K = 70), Vestolit S7054 | 100 parts by weight |
| Epoxidised soybean oil | 10 parts by weight |
| Ca—Zn stabiliser | 2 parts by weight |
| Chelator | 0.5 parts by weight |
| Antifogging agent sorbitan laurate | 1.0 parts by weight |
| Polyoxyethylene alkyl ether | 1.0 parts by weight |
| Plasticiser composition | 35 parts by weight |

Test Procedure

The above formulation is moulded into a wrap film by use of a 19 mm extruder and the film is subjected to tests for evaluation of properties.

Specifications of Extruder

A Brabender extrusiograph Type 19/25 D Screw diameter 19 mm, L/D=25, die 25 mm wide die Screw compression ration 2:1

| Extrusion Conditions | |
|---|---|
| Cylinder head temperature | 195° C. |
| Die temperature | 205° C. |
| Screw speed | 35 rpm |
| Take-off speed | 12 m/min |

The test procedure demonstrates that Composition B provides a polymer composition having good processability, good transparency, bleeding and antifogging properties.

Example 5

Each of the six compounds being evaluated were incorporated in PVC.

The compounds were incorporated in the PVC in the following amounts.

| PVC (K = 70), Solvic S 271 GC* | 100 parts by weight |
|---|---|
| Plasticiser | 40 parts by weight |

*available from Solvay & Cie, Belgium

The PVC and plasticiser compounds were mixed in a Brabender Planetary Mixer Type P 600. The mixer was operated at 88° C. and 100 RPM. The procedure is in accordance with ISO/DIS 4574.

The individual compounds are compression moulded into sheets having a thickness of approximately 4 mm in accordance with ISO 293-1974. Conditions were 190° C. and an applied pressure of 7.5 bar. Moulding time was set to 150 seconds.

Dumbbell test specimens were cut from the compression moulded sheets according to DIN 53457 Dumbbell no. 4). The properties measured to evaluate the plasticiser effect are shown in the table below. Shore A was measured according to DIN 53505. All other properties were recorded in accordance with DIN 53457.

| | Results | | | | | |
|---|---|---|---|---|---|---|
| Plasticser | Youngs Modulus [Mpa] | Strain at Break [%] | Stress at Break [MPa] | Shore A (after 3 sec.) | Shore A (after 15 sec.) | SASE (100%) [Mpa] |
| DOP | 12.04 | 639.3 | 22.20 | 92.5 | 90.0 | 8.46 |
| DINP | 15.04 | 687.4 | 24.06 | 94.0 | 91.5 | 9.31 |
| Compound A | 16.14 | 678.7 | 28.01 | 91.0 | 88.0 | 10.40 |
| Compound B | 12.96 | 733.0 | 24.98 | 91.0 | 88.0 | 9.07 |
| Compound C | 25.89 | 690.4 | 23.83 | 95.0 | 92.0 | 10.51 |
| Compound D | 101.20 | 474.8 | 19.89 | 98.0 | 97.0 | 12.88 |

The parameters typically used to describe the plasticising effect is Young's Modulus and Shore A values.

Young's Modulus is also called the elasticity modulus and the lower the value of this parameter the better is the plasticising effect.

Shore A is a measure of the hardness of the product. This value should in general be as low as possible.

The stress required for a 100% elongation of the test specimen (SASE, 100%) is also used to evaluate the properties of a plasticiser. A low value on this parameter indicates a good plasticising effect.

The "Strain at Break" and "Stress at Break" are two additional mechanical properties that are used to describe a plasticised PVC.

In comparison to the industry standard plasticiser DOP, Compound B provided analogous performance to DOP. Compound 8 provided superior performance when compared to Compound A and DINP. Compound C and D exhibited a plasticising effect but exhibited inferior performance compared to Compound B.

Example 6

Each of the six compounds being evaluated were incorporated in PVC.

The compounds were prepared in accordance with Example 5 and incorporated in the PVC in the following amounts.

| PVC (K = 70), Solvic S 271 GC* | 100 parts by weight |
|---|---|
| Plasticiser | 60 parts by weight |

*available from Solvay & Cie, Belgium

| Plasticiser | Youngs Modulus [Mpa] | Strain at Break [%] | Stress at Break [MPa] | Shore A (after 3 sec.) | Shore A (after 15 sec.) | SASE (100%) [Mpa] |
|---|---|---|---|---|---|---|
| DOP | 3.87 | 878.4 | 17.71 | 79.0 | 76.5 | 3.81 |
| DINP | 4.46 | 882.0 | 19.15 | 83.5 | 80.0 | 4.31 |
| Compound A | 4.99 | 815.0 | 18.49 | 79.0 | 75.5 | 4.70 |
| Compound B | 4.19 | 868.2 | 18.42 | 80.5 | 76.0 | 3.88 |
| Compound C | 6.65 | 756.0 | 18.05 | 88.0 | 85.0 | 5.48 |
| Compound D | 64.43 | 487.5 | 18.23 | 97.0 | 93.5 | 10.73 |

Results for this formulation which contains 60 parts plasticiser shows a better plasticising effect for all products in comparison to the results obtained with the formulation of Example 5 (40 pants plasticiser).

As for Example 5 in comparison to industry standard DOP, Compound B provided analogous performance to DOP, in particular in respect of Young's Modulus, SASE (100%) and Shore A. Compound B provided superior performance when compared to Compound A and DINP. Compound C and D exhibited a plasticising effect but exhibit inferior performance than Compound B.

All publications mentioned in the above specification are herein incorporated by reference. Various modifications and variations of the described methods and system of the invention sill be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

What is claimed is:

1. A composition comprising
    i) a thermoplastic polymer
    ii) a compound having the formula

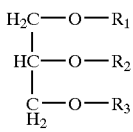

wherein $R_1$, $R_2$ and $R_3$ are independently selected from an acyl group or a hydrogen atom,
wherein at least one of $R_1$, $R_2$ and $R_3$ is an acyl group (a short acyl group) having from 2 to 6 carbon atoms
wherein at least one of $R_1$, $R_2$ and $R_3$ is a branched chain acyl group (a long acyl group) having a saturated chain having 10 to 20 carbon atoms and a hydrophilic branch group.

2. A composition according to claim 1 wherein the hydrophilic branch group is an acyl group or a derivative thereof.

3. A composition according to claim 2 wherein the hydrophilic branch group is a group of the formula

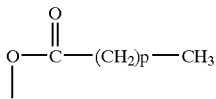

wherein p is from 0 to 4.

4. A composition according to claim 1 wherein two of $R_1$, $R_2$ and $R_3$ are the short acyl groups and wherein the other of $R_1$, $R_2$ and $R_3$ is a long acyl group.

5. A composition according to claim 1 wherein the chain of the long acyl group has a chain having 14 to 20 carbon atoms.

6. A composition according to claim 5 wherein the chain of the long acyl group consists of a chain having 16 to 20 carbon atoms.

7. A composition according to claim 1 wherein the short acyl group is an acyl group having from 2 to 5 carbon atoms.

8. A composition according to claim 7 wherein the short acyl group is an acyl group having 2 carbon atoms.

9. A composition according to claim 1 wherein the short acyl group is present in an amount, on average, of no greater than 2 moles per mole of glycerol and esters thereof.

10. A composition according to claim 1 wherein the long acyl group is present in an amount, an average, of at least 0.4 moles, preferably from 0.9 to 2 moles, more preferably from 0.9 to 1 moles per mole of glycerol and esters thereof.

11. A composition according to claim 1 wherein the total amount of the acyl groups is, on average, 2.7 to 3.0 moles per mole of glycerol and esters thereof.

12. A composition according to claim 1 wherein the compound is an acetylated interesterification product of glycerol and an oil selected from castor oil, including hardened castor oil, unhardened castor oil and mixtures thereof.

13. A composition according to claim 1 wherein the thermoplastic polymer is or comprises a vinyl chloride polymer or a vinyl chloride copolymer selected from vinyl chloride/vinyl acetate copolymer, vinyl chloride/vinylidene chloride copolymer, vinyl chloride/ethylene copolymer and a copolymer prepared by grafting vinyl chloride onto ethylene/vinyl acetate copolymer, and mixtures thereof.

14. A composition according to claim 1 wherein the thermoplastic polymer is or comprises a polymer blend of a thermoplastic polymer and a second polymer.

15. A composition according to claim 14, wherein the second polymer is a methacryl polymer or an acrylonitrile-butadiene-styrene polymer.

16. A composition according to claim 1 wherein the composition comprises the compound in an amount of 1 to 100 parts by weight per 100 parts by weight of the thermoplastic polymer.

17. A composition according to claim 1 wherein the compound has the formula

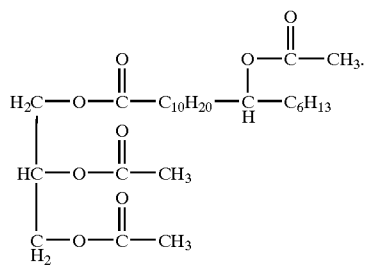

18. A composition according to claim 1 wherein the compound has the formula

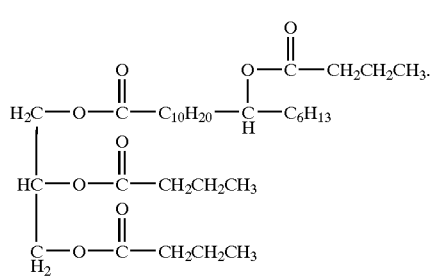

19. A composition according to claim 1 wherein the compound has the formula

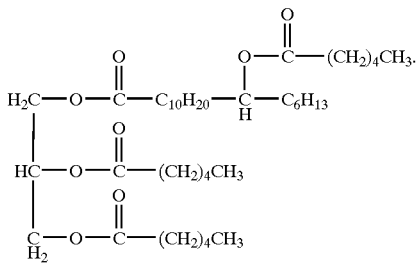

20. A composition comprising a compound according to the formula

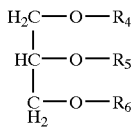

wherein two of $R_4$, $R_5$, and $R_6$ of the formula

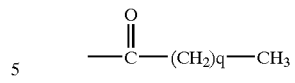

wherein for each of the two of $R_4$, $R_5$, and $R_6$, q is independently selected from 0 to 3 and the other of $R_4$, $R_5$, and $R_6$ is a branched group of the formula

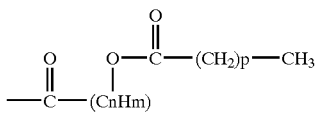

wherein n is from 10 to 20 and m is 2n, and wherein p is from 0 to 4, and a thermoplastic polymer.

* * * * *